(12) United States Patent
Maurer

(10) Patent No.: US 9,134,206 B2
(45) Date of Patent: Sep. 15, 2015

(54) CONTAINER FOR NON-INVASIVE FLUID SAMPLE ACCESS

(75) Inventor: Elisabeth Maurer, Vancouver (CA)

(73) Assignee: Canadian Blood Services, Ottawa, Ontario (CA)

( * ) Notice: Subject to any disclaimer, the term of this patent is extended or adjusted under 35 U.S.C. 154(b) by 415 days.

(21) Appl. No.: 13/817,877

(22) PCT Filed: Aug. 31, 2011

(86) PCT No.: PCT/CA2011/050530
§ 371 (c)(1),
(2), (4) Date: Feb. 20, 2013

(87) PCT Pub. No.: WO2012/027847
PCT Pub. Date: Mar. 8, 2012

(65) Prior Publication Data
US 2013/0145868 A1    Jun. 13, 2013

Related U.S. Application Data

(60) Provisional application No. 61/378,693, filed on Aug. 31, 2010.

(51) Int. Cl.
*G01N 1/00*      (2006.01)
*G01N 1/28*      (2006.01)
*B01L 3/00*      (2006.01)
*G01N 21/03*     (2006.01)
*G01N 21/51*     (2006.01)

(52) U.S. Cl.
CPC . *G01N 1/28* (2013.01); *B01L 3/505* (2013.01); *G01N 21/03* (2013.01); *B01L 2200/141* (2013.01); *B01L 2200/143* (2013.01); *B01L 2300/044* (2013.01); *B01L 2300/047* (2013.01); *B01L 2400/0481* (2013.01); *B01L 2400/0638* (2013.01); *G01N 2021/0346* (2013.01); *G01N 2021/0364* (2013.01); *G01N 2021/513* (2013.01)

(58) Field of Classification Search
None
See application file for complete search history.

(56) References Cited

U.S. PATENT DOCUMENTS 4,411,358 A * 10/1983 Bennwik et al. .............. 206/771

* cited by examiner

*Primary Examiner* — Robert R Raevis
(74) *Attorney, Agent, or Firm* — Hancock Hughey LLP

(57) ABSTRACT

A deformable container (5) containing a fluid product to be tested includes a flexible outer wall (10) enclosing a main cavity (9) therein for holding the fluid product and at least one appendix (14) for containing a sample volume to be tested. The appendix is displaceable from a first position, wherein the appendix is invaginated within a periphery of the deformable container, and a second position, wherein the appendix protrudes outwardly from the outer wall and defines a second cavity (7) therein for a sample fluid volume, such as to permit testing of the sample volume within the appendix (14). The appendix is displaced into the second position by the fluid product within the deformable container when pressure is applied to the outer wall to force the sample volume of the fluid product from the main cavity of the deformable container into the second cavity of the appendix.

26 Claims, 6 Drawing Sheets

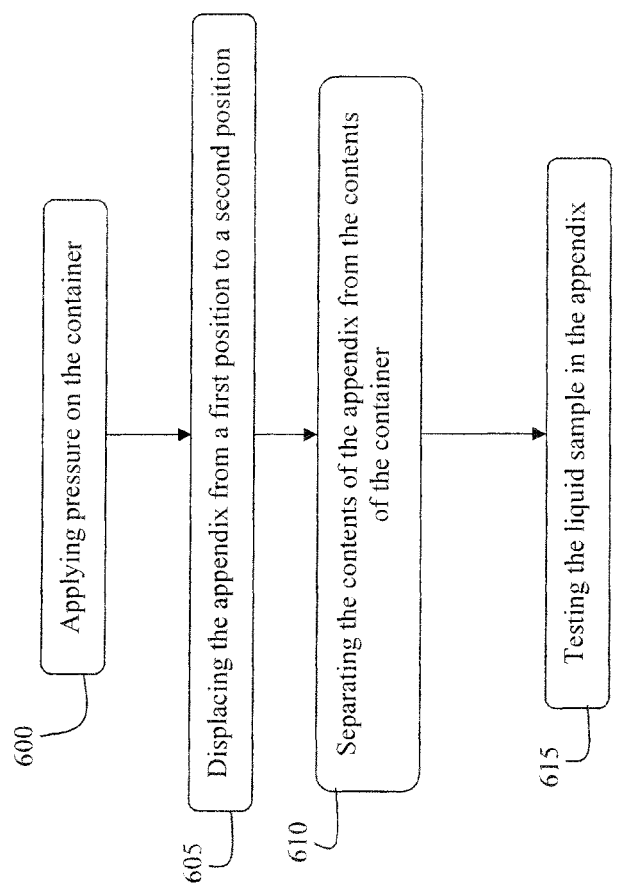

US 9,134,206 B2

CONTAINER FOR NON-INVASIVE FLUID SAMPLE ACCESS

CROSS-REFERENCE TO RELATED APPLICATIONS

This application claims priority on U.S. patent application Ser. No. 61/378,693 filed Aug. 31, 2010, the entire content of which is incorporated herein by reference.

TECHNICAL FIELD

The invention relates generally to containers for fluid samples, and more particularly to containers permitting non-invasive sample access for testing purposes.

BACKGROUND

Optical analysis devices which test a fluid sample for selected particles, constituent elements or other characteristics, are well known. The fluid sample being tested is typically contained within a translucent container, such as a clear glass or plastic capillary or cuvette, which is in turn held in position by an associated sample holder, also known as a capillary holder or cuvette holder.

The optical analysis device carries out an analysis such as dynamic light scattering, where an optical source such as laser light is focused throughout the container and into the fluid sample. The laser light scatters on particles in the fluid sample, and the scattered light is then collected by light collectors disposed at specific angles relative to the laser light. The scattered light fluctuates based on the concentration of the particles in suspension and their random Brownian movement. The optical analysis device thus generates a spectrographic analysis of the fluid sample based on the scattered light.

However, as the optical device performs such an analysis, the quality of fluid sample contained in the containers may decrease or the spectrographic analysis may provide erroneous results. Further, when platelet concentrate is the fluid to be stored and tested, the storage container for such platelet concentrates cannot be clear plastic or glass, and therefore a sample of the platelet concentrate has to be extracted from the main storage container or reservoir and placed into another compartment that is suitable for optical testing. However, this transfer of sample by non-invasive means such that the sample remains sterile is difficult, often time consuming and costly. There is therefore a need for a device which will permit the simple transfer of a fluid sample into an optically suitable sample compartment.

Therefore, there is a need for an improved container for use in the testing of fluid samples.

SUMMARY

In accordance with one aspect of the present invention, there is provided a deformable container adapted to contain a liquid product to be tested by a testing device, the deformable container comprising: an impermeable and flexible outer wall defining a periphery of the deformable container and enclosing a main cavity therein for holding the liquid product; and at least one impermeable appendix for containing a sample volume of the liquid product to be tested, the appendix having an invertible wall that is integrally formed with the outer wall, the appendix being displaceable between a first position wherein the appendix is invaginated within the periphery of the deformable container and a second position wherein the appendix protrudes outwardly from the outer wall such as to permit testing of the sample volume therewithin using the testing device; wherein in said second position the invertible wall of the protruding appendix defines a second cavity therein that is smaller than the main cavity and in fluid flow communication therewith, the second cavity being filled with the liquid product when the appendix is displaced from the first position to the second position, the appendix being displaced into the second position by the liquid product within the deformable container when pressure is applied to the outer wall to force the sample volume of the liquid product from the main cavity of the deformable container into the second cavity of the appendix.

In accordance with another aspect of the present invention, there is provided a method for non-invasively testing a sample of a liquid contained in a deformable container, the method comprising: applying pressure on an outer flexible wall of the deformable container, the deformable container having an appendix to be filled with the sample of the liquid to be tested, the applied pressure on the outer flexible wall displacing the appendix from a first position, wherein the appendix is invaginated within the outer wall, to a second position, wherein the appendix protrudes from the outer wall, the appendix in said second position having the sample of the liquid to be tested enclosed therewithin; and testing the sample of the liquid product within the appendix using a testing device.

There is further provided, in accordance with a further aspect of the present invention, a method of hermetically withdrawing a sample of a fluid to be tested from a container containing said fluid, the method comprising: providing the container with a deformable outer wall and an invaginated appendix to be filled with the fluid sample; displacing the invaginated appendix of the container into an outwardly extending position, wherein the appendix protrudes from the deformable outer wall of the container, by applying pressure on the deformable outer wall of the container to force the sample of the fluid to be tested into the appendix; and sealing the appendix from a remainder of the container to thereby seal the fluid sample to be tested within the protruding appendix.

BRIEF DESCRIPTION OF THE DRAWINGS

Further features and advantages of the present invention will become apparent from the following detailed description in conjunction with the appended drawings, in which:

FIG. 6 illustrates a flow chart of a method for testing a fluid sample using the container of the present disclosure.

It will be noted that throughout the appended drawings, like features are identified by like reference numerals.

DETAILED DESCRIPTION

Figure 1:
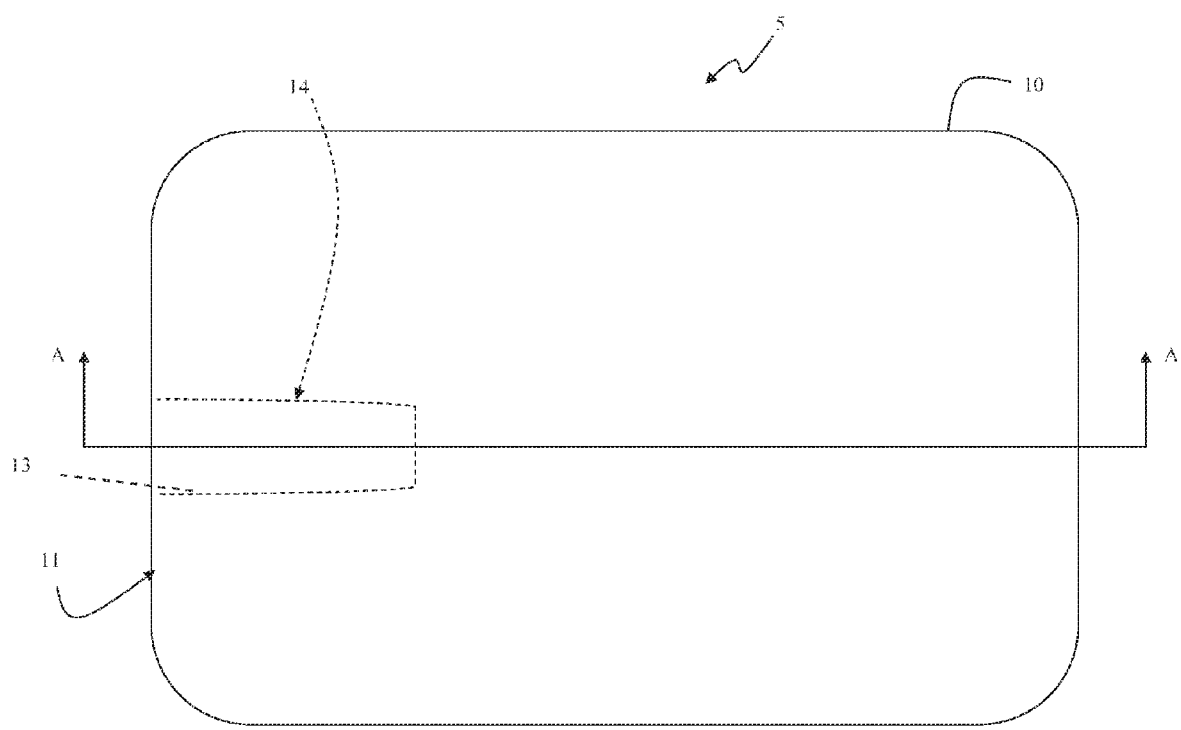
FIG. 1 is a top plan view of a container in accordance with a first embodiment, having a detachable fluid sample appendix in a first, invaginated, position.

Referring to FIG. 1, a fluid container 5 which is at least partially deformable comprises a flexible outer wall 10 that forms the periphery of the container and defines therein a main cavity 9 within which the fluid product contained in the container is enclosed. At least a portion of the outer wall 10 is sufficiently flexible such that a manual pressure applied thereto from outside the container will cause the appendix 14 to be expressed outwardly and thus cause the fluid within the main cavity 9 to be displaced, as noted in further detail below, into to second smaller cavity 7 (see, e.g., FIG. 4) within the appendix 14. The outer wall 10 is impermeable such that a fluid, for example a biological liquid such as blood, blood plasma, platelet concentrate, etc., may be contained therein. The container 5 may be a capillary container or a cuvette, adapted to contain a sample of a liquid product. The outer wall 10 of the container 5 is made of a flexible and deformable material, such as a plastic, vinyl (ex: ethylene vinyl acetate) polyvinyl chloride), a thermoplastic polymer (ex: polypropylene) or another suitable flexible and/or bag-like material, provided the material chosen for the container 5 is sufficiently flexible to permit deformation of the outer wall 10 an amount necessary to displace the liquid therein into an appendix 14 region, as will be described in further detail below. The outer wall 10 may also be made of a translucent material which is sufficiently transparent to allow light to be focused throughout the container. The liquid product enclosed within the container can be blood or any other fluid to be tested, optically or otherwise, for example in order to identify particular particles in suspension such as platelets, nano-particles, etc.

Figure 3:
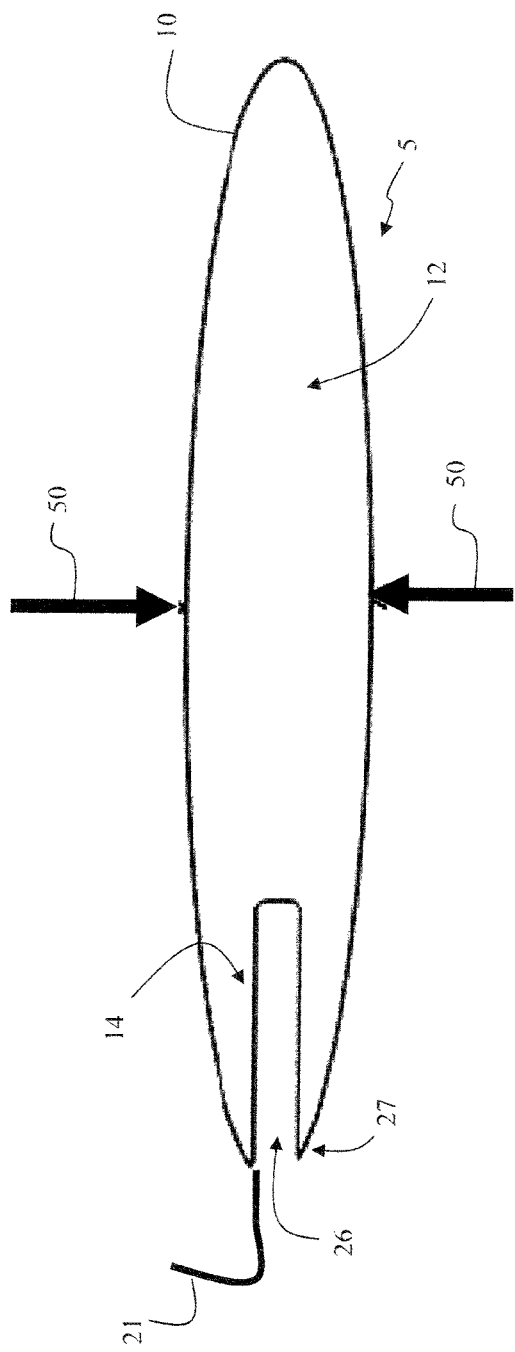
FIG. 3 is a longitudinal cross-sectional view of the container of FIG. 1, taken along line A-A, wherein pressure is being applied to the container.
Figure 4:
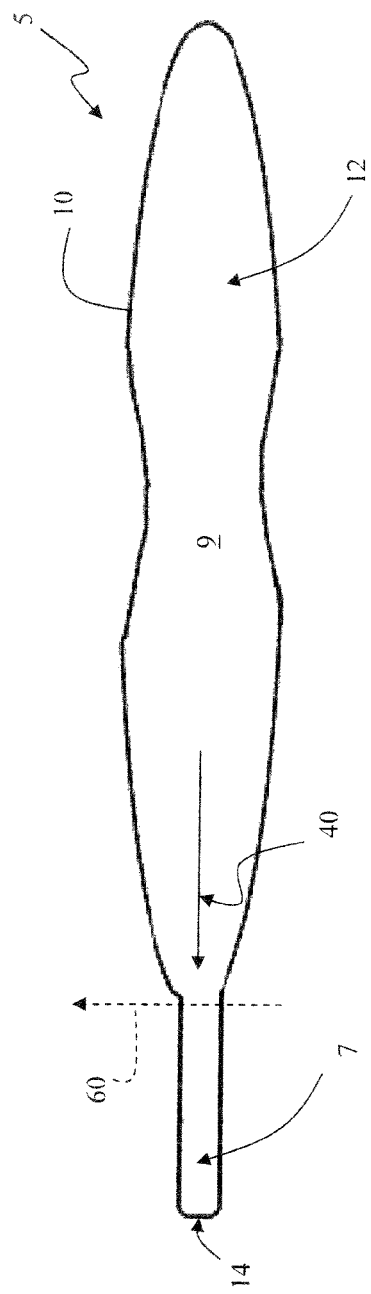
FIG. 4 is a longitudinal cross-section view of the container of FIG. 1 taken along line A-A, showing the detachable fluid sample appendix being in a second, extended, position.

As seen in FIG. 1, the container 5 includes an appendix 14 which is formed in a longitudinal end 11 of the container and defines a cross-sectional area that is less than that of the entire container 5, and therefore also has a volume that is smaller than that of the container 5. The appendix 14 includes an invertible wall 13 which that is integrally formed with the outer wall 10 of the remainder of the container. As will be seen, the invertible wall 13 of the appendix 14 is sufficiently flexible to permit the entire appendix 14 to invert, such as to go from an invaginated position as shown in FIG. 3 to an extended and protruding position as shown in FIG. 4. The appendix 14 is at least initially disposed in a first, retracted or invaginated, position as seen in FIG. 1, wherein the appendix 14 is inverted and extends inwardly from periphery of the outer wall 10 and thus protrudes into the cavity of the container 5.

Figure 2:
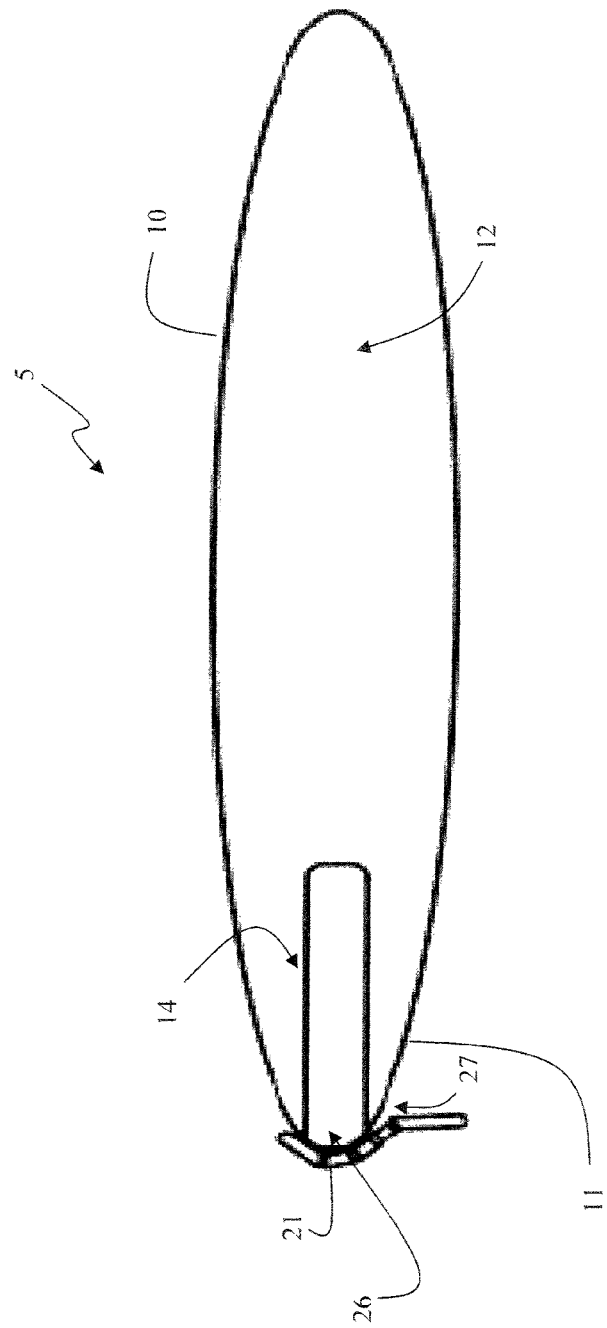
FIG. 2 is a longitudinal cross-sectional view of the container of FIG. 1, taken along line A-A.

Referring to FIG. 2, a retaining mechanism which maintains the appendix in the first, invaginated, position until a predetermined level of pressure is applied to the outer wall of the container. This retaining mechanism may include, for example, a latch member 21 that is engaged to the end 11 of the container 5 overtop of the opening formed in the outer wall 10 by the appendix 14 when disposed in the invaginated position. The latch member 21 is releasably fastened to at least a first latching end 27 on the deformable container 5, such that the latch member 21 can be displaced from a locked position (as seen in FIG. 2) to an open position away from the opening 26 (as seen in FIG. 3). This open position of the latch member 21 thus permits the appendix 14 to be displaced into its extended position (as shown in FIG. 4), by inverting itself, as will be described further below. When the latch member 21 is in its locked position, as shown in FIG. 2, the latch member maintains the appendix 14 invaginated within the container 5. The latch member 21 can be tape or other suitable enclosing flap, which is secured to the end 11 of the container with sufficient force to maintain the appendix 14 in the first, invaginated, position as seen in FIG. 2. It is of note that although the appendix 14 is depicted in the figures as being invaginated within the end 11 of the container 5, it is to be understood that the appendix 14 may be located any suitable location within the outer wall 10 of the container 5. For example, the appendix 14 can be placed within the bottom of the container 5 or elsewhere the within a side wall of the container 5.

Referring to FIG. 3, the latch member 21 is shown in its released position, such that the latch member 21 is disconnected from at least the first latching end 27 to expose the opening 26 formed at the junction between the appendix 14 and the main outer wall 10 of the container. Alternately, however, the latch member 21 may be disconnected from both sides of the opening 26 such that the latch member 21 is completely detached from the container 5. As noted above, the latch member 21 may be manually detached by a user of the container 5 or alternately, the adhesive or other fastening force retaining the latch member 21 to the outer wall at the first latching end 27 thereof may be selected such that the latch member remains in place (and therefore retains the appendix 14 in its invaginated position) when the container 50 is uncompressed but detaches from at least the first latching end 27 when pressure 50 is applied on the outer wall 10.

Regardless of the manner by which the latch member 21 is opened, as shown in FIG. 3, the appendix 14 is displaced from its first, invaginated, position as seen in FIG. 3 to its second, extended, position as seen in FIG. 4 in the following manner. The pressure 50 applied to the outer wall 10 of the container 5 causes the flexible outer walls to move inwardly, thereby displacing the liquid product 12 within the container 5 and forcing the invaginated appendix 14 to invert upon itself and thus fill with the liquid product in the process. This accordingly forces the appendix 14 to be displaced into its extended position (FIG. 4) whereby it protrudes outwardly, into this second position, beyond the previously defined periphery of the outer wall 10 of the container 5. The pressure 50 can be manually applied on the outer wall 10, for example by simply squeezing the deformable container 5 using one's hand. Alternatively, the pressure 50 can be mechanically applied using a suitable apparatus or a device, wherein the container 5 is compressed, for example by a clamping mechanism. In FIG. 3, the pressure 50 is shown to be applied on opposite sides of the container in a substantially equal amount, however it is to be understood that the pressure may be applied in other manners (for example, from one direction only, etc.).

In FIG. 4, the appendix 14 is shown in its extended position, wherein the liquid product 12 is displaced in the direction 40 from the main cavity defined by the outer walls 10 of the container into the smaller cavity formed within the extended appendix 14.

Once the appendix 14 has been expressed in its extended position as shown in FIG. 4, it may be separated or otherwise severed from the remainder of the container 5. This may be achieved, for example only, using a heat sealing device which permits the appendix 14 to be severed from the remainder of the container 5 while simultaneously sealing both the now-separate appendix 14 and the main container 5. The heat sealing device my use a laser for this purpose, for example, to simultaneously cut and seal the expressed appendix 14 from the container 5, for example, along cut line 60. This seals both the container 5 and the expressed appendix 14, both of which now contain the liquid product 12 hermetically therein. Therefore, spillage and contamination of the liquid product 12 may thus be avoided. Furthermore, the separation of the appendix 14 from the container 5 may make the testing of the sample in the appendix simpler to carry out. The testing may include an optical analysis, such as spectroscopic tests for example, with a suitable optical testing device. The optical analysis may consist of Dynamic Light Scattering (DLS), where incident light is focused throughout the transparent and/or translucent walls of the appendix 14, now containing a smaller sample of the liquid product 12 than the main container 5.

The testing device can be a medical device or a non-medical device, for example one used for the testing of food products, consumable and non-consumable liquids, and the like. In one particular embodiment the test performed on the fluid within the appendix 14 is an optical test, and therefore the testing instrument is an optical test device of the type, for example, that uses an optical source such as laser light to be focused throughout the appendix 14 and into the liquid product 12. However, other testing instruments can also be used, both optical and non-optical, to perform the desired analysis of the fluid contained within the appendix 14, whether this appendix 14 is severed from the container or not. In the particular case of an optical test being performed on the fluid within the appendix 14, the laser light scatters on particles in the liquid product 12, and the scattered light is then collected by light collectors disposed at specific angles relative to the laser light. The scattered light fluctuates based on the concentration of the particles in suspension. Using algorithms, these fluctuations of scattered light are then correlated to the particles' mean size, shape and/or other properties, and for example may include or be expressed in terms of hydrodynamic radius.

As the testing device may require heat transfer to and from the container 5, the quality of the liquid product may decrease and the liquid product may be unusable. Therefore, separating the appendix 14 from the container 5 may be performed to prevent the whole container 5 from needing to be exposed to changes in temperatures which may occur during such an optical analysis testing, and thus may maintain the quality of the liquid product. As an example, quality preservation can be provided when multiple tests are carried out on a same container 5. In this example, heat transfer to and from the liquid product 12 will be made on the liquid product contained within the detached appendix 14, without needing to expose the remainder of the fluid in the container. In the case of blood testing, the quality of platelets may accordingly be preserved with the use of the separated appendix 14 containing a blood sample. The quality of the platelets may then be preserved for blood transfusions from the container 5. However, it is to be understood that it is equally possible to keep the protruding appending 14 attached to the container 5 during the testing of the liquid contained within the appendix 14. As such, a seal (such as a heat seal, for example) may be formed between the container 5 and the appendix 14 to seal the sample of liquid to be tested within the appendix 14. Testing can then be performed on the liquid sample within the appendix 14, with the appendix remaining attached to the remainder of the container. This may in some cases be logistically easier, whereby the appendix is only detached from the container after the measurement and/or testing on the liquid sample is completed, to preserve the identity of the appendix. For example, in one scenario, the appendix is heat sealed but still remains attached to the container until after the analysis, while still only exposing the sample in the appendix to the required temperature change or other treatments (irradiation, etc.). The length of the appendix 14 and the size and type of seal formed between the appendix 14 and the container 5 can also be varied as needed in this respect, such that the contents of the container remain un-affected by temperature, etc. to which the sample in the appendix is exposed.

Accordingly, the container described herein permits a "non-invasive" access to the fluid enclosed within the container, in that a small sample of the fluid can be hermetically withdrawn from the container, via the appendix 14 as described above, without needing to open the container or otherwise break the seal enclosing the remaining fluid within the container, and therefore also without risking contamination of either the withdrawn fluid sample (i.e. within the appendix) or the remaining fluid in the container. This is true whether the appendix 14 is severed from the rest of the container 5 or not.

Figure 5:
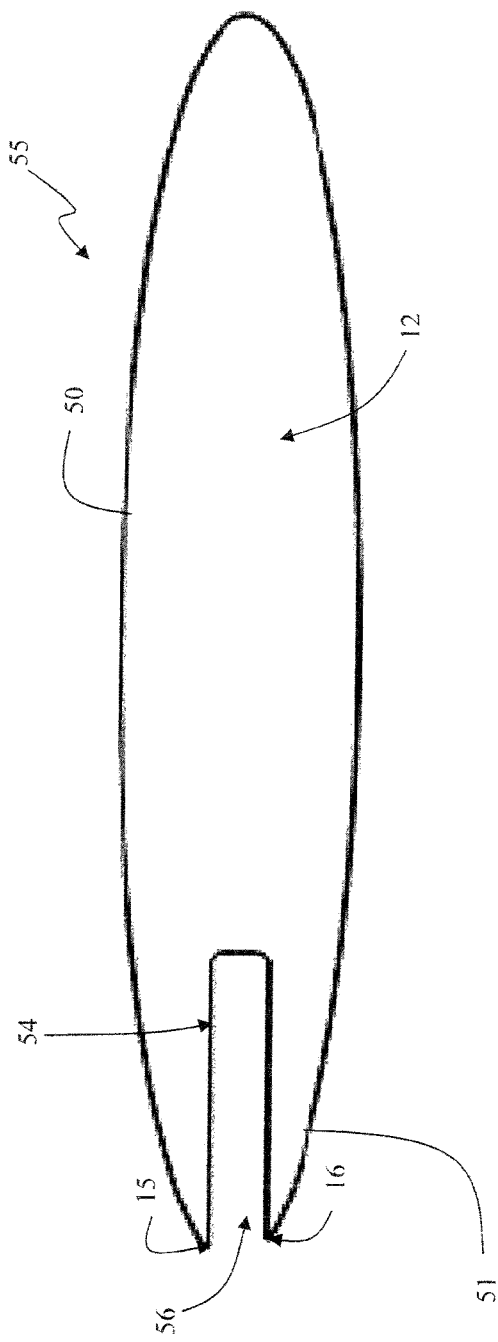
FIG. 5 is a longitudinal cross-sectional view of a container in accordance with an alternate embodiment.

Referring to FIG. 5, a container 55 of an alternate embodiment is shown. The container 55 comprises an outer wall 50 that defines the periphery of the container 55, the outer wall 50 being made of a translucent and deformable material which is sufficiently transparent to allow the liquid product 12 to be tested with a testing device that carries out optical analysis, such as a dynamic light scattering device for example. Similar to the container 5 described above, the container 55 comprises an invaginated appendix 54 defined by the outer wall 50. However, contrary to the container 5, the container 55 of the present embodiment maintains itself in an invaginated position, without the need of a latch. While the container 55 still includes a retaining mechanism which maintains the appendix in the first, invaginated, position until a predetermined level of pressure is applied to the outer wall of the container, in this embodiment the retaining mechanism includes one or more reinforced regions of the container, for example at the junction between the periphery of the outer wall and the appendix. The appendix 54 is maintained in the first retracted, or invaginated, position within the container 55 by these reinforced regions or junctions 15 and 16 integrally formed in the end 51 of the outer wall 50 of the container 55 in which the opening 56 located, prior to the inversion of the appendix 54. The reinforced junctions 15 and 16, and the outer wall 50 can be made with the same deformable material as discussed for the outer wall 10, however the reinforced junctions 15,16 provide greater rigidity such that the appendix 54 is maintained in its retracted position (as shown in FIG. 5) until pressure is applied to the outer wall 50 of the container 55. When such a pressure is applied to the outer wall 50, for example but not necessarily transversely in opposite directions simultaneously as shown in FIG. 3, the appendix 54 is expressed outwardly into its second, or extended position as the result of the pressure applied to the outer wall of the deformable container. As per the embodiment described above, when the appendix 54 is disposed in the second, extended, position it protrudes outwardly beyond the outer wall in a manner similar to that shown in FIG. 4. The fluid within the container thereby fills the appendix 54 when disposed in its extended position, such that the fluid sample within the appendix portion can then be tested with an optical testing device, such as a dynamic light scattering device. As noted above, this optical testing device may be used for medical purposes, or otherwise (such as for food analysis, etc.).

Referring to FIG. 6, one particular embodiment of the method for testing of a sample of the liquid product 12 contained in the container 5 includes at least a first step 600 of applying pressure on the container 5, a second step 605 of displacing the appendix 14 of the container 5 from a first position to a second position. Optionally, the method as described herein may also optionally include a third step 610 of separating content of the appendix 14 from that of the container 5, and a fourth step 615 of testing the liquid product 12 in the appendix 14. The first and second steps 600 and 605 may, however, be a single operation given that the step 600 of applying pressure on the container outer walls forces the appendix from its first position to its second position, as defined in step 605. It is to be understood that the third step 610, namely separating the content of the appendix from that of the container, may include actually separating the appendix from the container, or maintaining the appendix attached to the container but simply sealing, and thus dividing, the sample volume of the liquid to be testing in the appendix from the rest of the liquid content of the container. If the fourth step 615 is carried out, this testing of the liquid sample within the appendix can therefore be conducted while the appendix remains attached to the container, or alternately, after the appendix has been severed from the container.

The first and/or second step 600,605 may further include releasing the latch 21 one or more latching points on the container wall. The step 605 causes the appendix 14 to be expressed outwardly such as to protrude beyond the outer wall 10. The step 610 may further include sealing the separated appendix 14 and the container 5, either simultaneously with, or immediately following, the separation of the appendix from the container. The separation and sealing process may be performed using a heat sealing device, which simultaneously severs the appendix and forms a seal on either side of the cut line such as to seal both the severed appendix and the container. The testing step 615 may include performing an optical analysis on the liquid product within the appendix, and may more particularly include performing a dynamic light scattering (DLS) measurement on the liquid sample.

Those skilled in the art will understand that the container 5 is not limited to the number appendixes shown on FIGS. 2 to 5. For example, the container 5 may comprise more than one appendix 14, and each of these appendices may be individually severed from the main container and sealed, thereby permitting several different samples of the liquid product to be separately tested. If desired, each of these appendices may have a separate latch 21, which may require manual disengagement for example, such that after one appendix 14 has been separated from the container 5, another latch can be released and pressure can be reapplied on the container 5 to force another expressed appendix 14 to protrude from the container 5, and either be severed for analysis of the sample within the severed appendix or alternately directly tested and/or measured in situ within the protruding appendix. Furthermore, it can be understood that these appendices may be individually or collectively displaceable from the first, invaginated, position to the second, extended, position, and vice versa.

The embodiments described above are intended to be exemplary only. The scope of the invention is therefore intended to be limited solely by the scope of the appended claims.

The invention claimed is:

1. A deformable container adapted to contain a liquid product to be tested by a testing device, the deformable container comprising:
    an impermeable and flexible outer wall defining a periphery of the deformable container and enclosing a main cavity therein for holding the liquid product, said main cavity defining a main cavity volume; and
    at least one impermeable appendix for containing a sample volume of the liquid product to be tested, the appendix having an invertible wall that is integrally formed with the outer wall, the appendix being displaceable between a first position wherein the appendix is invaginated within the periphery of the deformable container and a second position wherein the appendix protrudes outwardly from the outer wall such as to permit testing of the sample volume therewithin using the testing device; wherein in said second position the invertible wall of the protruding appendix defines a second cavity therein that is at all times smaller than the main cavity and in fluid flow communication therewith, the second cavity being filled with the liquid product when the appendix is displaced from the first position to the second position, the appendix being displaced into the second position by the liquid product within the deformable container when pressure is applied to the outer wall to force the sample volume of the liquid product from the main cavity of the deformable container into the second cavity of the appendix.

2. The deformable container of claim 1, wherein at least a portion of the invertible wall of the appendix is made of a translucent material sufficiently transparent to allow non-invasive optical analysis of the sample volume of the liquid product within the appendix.

3. The deformable container of claim 2, wherein the appendix is detachable from the deformable container once disposed in the second position.

4. The deformable container of claim 3, wherein the appendix is sealable such as to separate the sample volume of the liquid product within the second cavity of the appendix from a remainder of the liquid product within the main cavity of the deformable container.

5. The deformable container of claim 4, wherein the appendix is severable from the outer wall once the appendix is sealed to enclose the second cavity.

6. The deformable container of claim 1, further comprising a retaining mechanism which maintains the appendix in the first position until a predetermined level of said pressure is applied to the outer wall of the container.

7. The deformable container of claim 6, wherein the retaining mechanism includes a latch member releasably fastened to the outer wall at a location thereon corresponding to the appendix, the latch member being displaceable from a locked position, wherein the appendix is retained in the first position, to an open position, wherein at least a portion of the latch member is detached from the outer wall to expose the appendix and thereby allow the appendix to be expressed outwardly into the second position thereof.

8. The deformable container of claim 6, wherein the retaining mechanism includes one or more reinforced regions of the container proximate a junction between the periphery of the outer wall and the appendix, the reinforced regions normally maintaining the appendix in the first position while allowing the appendix to be expressed outwardly into the second position thereof when the predetermined pressure level is applied to the outer wall of the container.

9. The deformable container of claim 1, wherein the appendix is disposed at a longitudinal end of the deformable container.

10. The deformable container of claim 1, wherein two or more of said appendices are disposed on the container, thereby permitting two or more of said samples to be drawn from the liquid product for separate testing.

11. A method for non-invasively testing a sample of a liquid contained in a deformable container, the method comprising:
    applying pressure on an outer flexible wall of the deformable container, the deformable container having an appendix to be filled with the sample of the liquid to be tested, the applied pressure on the outer flexible wall displacing the appendix from a first position, wherein the appendix is invaginated within the outer wall, to a second position, wherein the appendix protrudes from the outer wall, the appendix in said second position having the sample of the liquid to be tested enclosed therewithin;
    sealing the sample of the liquid within the appendix from a remainder of the liquid within the container; and testing the sample of the liquid product within the appendix using a testing device.

12. The method of claim 11, further comprising using a heat sealing device to seal the appendix.

13. The method of claim 11, further comprising, prior to the step of testing, severing the appendix filled with the sample from container.

14. The method of claim 13, wherein the step of testing further comprises performing an optical analysis of the sample of the liquid product within the appendix.

15. The method of claim 14, further comprising conducting a dynamic light scattering measurement on the sample.

16. The method of claim 11, wherein displacing the appendix into the second position further comprises releasing a latch member which retains the appendix in said first position until a predetermined level of said pressure is applied to the outer flexible wall of the container.

17. A method of hermetically withdrawing a sample of a fluid to be tested from a container containing said fluid, the method comprising:
providing the container with a deformable outer wall and an invaginated appendix to be filled with the fluid sample;
displacing the invaginated appendix of the container into an outwardly extending position, wherein the appendix protrudes from the deformable outer wall of the container, by applying pressure on the deformable outer wall of the container to force the sample of the fluid to be tested into the appendix; and
sealing the appendix from a remainder of the container to thereby seal the fluid sample to be tested within the protruding appendix.

18. The method of claim 17, further comprising severing the sealed appendix, filled with the fluid sample, from container.

19. The method of claim 18, further comprising testing the fluid sample within the appendix.

20. The method of claim 19, further comprising performing the step of testing after the step of sealing.

21. The method of claim 19, wherein the step of testing further comprises performing an optical analysis of the fluid sample within the appendix.

22. The method of claim 21, further comprising conducting a dynamic light scattering measurement on the fluid sample.

23. The method of claim 18, further comprising performing the steps of sealing and severing simultaneously using a heat sealing device.

24. A deformable container adapted to contain a liquid product to be tested by a testing device, the deformable container comprising:
an impermeable and flexible outer wall defining a periphery of the deformable container and enclosing a main cavity therein for holding the liquid product, said main cavity defining a main cavity volume; and
at least one impermeable appendix for containing a sample volume of the liquid product to be tested, the appendix having an invertible wall, at least a portion of which is made of a translucent material sufficiently transparent to allow non-invasive optical analysis of the sample volume of the liquid product within the appendix, said invertible wall being integrally formed with the outer wall, the appendix being displaceable between a first position wherein the appendix is invaginated within the periphery of the deformable container and a second position wherein the appendix protrudes outwardly from the outer wall such as to permit testing of the sample volume therewithin using the testing device;
wherein in said second position the invertible wall of the protruding appendix defines a second cavity therein that is smaller than the main cavity and in fluid flow communication therewith, the second cavity being filled with the liquid product when the appendix is displaced from the first position to the second position, the appendix being displaced into the second position by the liquid product within the deformable container when pressure is applied to the outer wall to force the sample volume of the liquid product from the main cavity of the deformable container into the second cavity of the appendix; and
wherein the appendix is detachable from the deformable container once disposed in the second position.

25. A deformable container adapted to contain a liquid product to be tested by a testing device, the deformable container comprising:
an impermeable and flexible outer wall defining a periphery of the deformable container and enclosing a main cavity therein for holding the liquid product, said main cavity defining a main cavity volume; and
at least one impermeable appendix for containing a sample volume of the liquid product to be tested, the appendix having an invertible wall that is integrally formed with the outer wall, the appendix being displaceable between a first position wherein the appendix is invaginated within the periphery of the deformable container and a second position wherein the appendix protrudes outwardly from the outer wall such as to permit testing of the sample volume therewithin using the testing device;
wherein in said second position the invertible wall of the protruding appendix defines a second cavity therein that is smaller than the main cavity and in fluid flow communication therewith, the second cavity being filled with the liquid product when the appendix is displaced from the first position to the second position, the appendix being displaced into the second position by the liquid product within the deformable container when pressure is applied to the outer wall to force the sample volume of the liquid product from the main cavity of the deformable container into the second cavity of the appendix; and
a retaining mechanism which maintains the appendix in the first position until a predetermined level of said pressure is applied to the outer wall of the container, said retaining mechanism including a latch member releasably fastened to the outer wall at a location thereon corresponding to the appendix, the latch member being displaceable from a locked position, wherein the appendix is retained in the first position, to an open position, wherein at least a portion of the latch member is detached from the outer wall to expose the appendix and thereby allow the appendix to be expressed outwardly into the second position thereof.

26. A deformable container adapted to contain a liquid product to be tested by a testing device, the deformable container comprising:
an impermeable and flexible outer wall defining a periphery of the deformable container and enclosing a main cavity therein for holding the liquid product, said main cavity defining a main cavity volume; and
two or more impermeable appendixes, each for containing a sample volume of the liquid product to be tested, each appendix having an invertible wall that is integrally formed with the outer wall and each appendix being displaceable between a first position wherein the appendix is invaginated within the periphery of the deformable container and a second position wherein the appendix protrudes outwardly from the outer wall such as to permit testing of the sample volume therewithin using the testing device;

wherein in said second position the invertible wall of the protruding appendix defines a second cavity therein that is smaller than the main cavity and in fluid flow communication therewith, the second cavity being filled with the liquid product when the appendix is displaced from the first position to the second position, the appendix being displaced into the second position by the liquid product within the deformable container when pressure is applied to the outer wall to force the sample volume of the liquid product from the main cavity of the deformable container into the second cavity of the appendix, said two or more appendixes permitting two or more of said samples to be drawn from the liquid product for separate testing.

* * * * *